United States Patent
Pepin et al.

(10) Patent No.: US 9,974,938 B2
(45) Date of Patent: May 22, 2018

(54) CUTTABLE CATHETER HUB WITH INTEGRATED HEMOSTASIS VALVE

(71) Applicant: Cardiac Pacemakers, Inc., St. Paul, MN (US)

(72) Inventors: Henry J. Pepin, Loretto, MN (US); John D. Kroeger, Mounds View, MN (US); Ronald Killins, Jr., Shoreview, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 556 days.

(21) Appl. No.: 14/561,211

(22) Filed: Dec. 4, 2014

(65) Prior Publication Data
US 2015/0157843 A1    Jun. 11, 2015

Related U.S. Application Data

(60) Provisional application No. 61/912,376, filed on Dec. 5, 2013.

(51) Int. Cl.
| | |
|---|---|
| *A61M 5/178* | (2006.01) |
| *A61M 39/06* | (2006.01) |
| *A61M 25/00* | (2006.01) |
| *A61M 25/06* | (2006.01) |
| *A61M 39/24* | (2006.01) |

(52) U.S. Cl.
CPC .... *A61M 39/0606* (2013.01); *A61M 25/0097* (2013.01); *A61M 25/0668* (2013.01); *A61M 39/06* (2013.01); *A61M 2025/0681* (2013.01); *A61M 2039/062* (2013.01); *A61M 2039/064* (2013.01); *A61M 2039/068* (2013.01);
(Continued)

(58) Field of Classification Search
CPC ...... A61M 25/0075; A61M 2025/0079; A61M 2039/0027; A61M 2039/0036; A61M 2039/00294; A61M 2039/064; A61M 2039/066
See application file for complete search history.

(56) References Cited

U.S. PATENT DOCUMENTS

| | | | |
|---|---|---|---|
| 4,634,432 A * | 1/1987 | Kocak | A61M 25/005 |
| | | | 137/846 |
| 5,613,956 A | 3/1997 | Patterson et al. | |

(Continued)

FOREIGN PATENT DOCUMENTS

| | | |
|---|---|---|
| EP | 2213327 A1 | 8/2010 |
| JP | 10500345 A | 1/1998 |

(Continued)

OTHER PUBLICATIONS

International Preliminary Report on Patentability issued in PCT/US2014/068673, dated Jun. 16, 2016, 8 pages.

(Continued)

*Primary Examiner* — Edelmira Bosques
(74) *Attorney, Agent, or Firm* — Faegre Baker Daniels LLP (57) ABSTRACT

A catheter hemostasis valve hub for a catheter or introducer sheath has a generally tubular shell with a first region and a second region having a greater thickness than the first region, a pre-slit hemostasis seal within the shell, and an end cap to retain the hemostasis seal within the shell having a web section. The hub is easily cut or slit after introduction of the catheter without prior breaking.

18 Claims, 9 Drawing Sheets

(52) U.S. Cl.
CPC ............... *A61M 2039/0653* (2013.01); *A61M 2039/2426* (2013.01)

(56) References Cited

U.S. PATENT DOCUMENTS

| | | |
|---|---|---|
| 6,551,283 B1 | 4/2003 | Guo et al. |
| 7,081,106 B1 | 7/2006 | Guo et al. |
| 7,101,353 B2 | 9/2006 | Lui et al. |
| 7,226,433 B2 | 6/2007 | Bonnette et al. |
| 7,241,276 B2 | 7/2007 | Argentine et al. |
| 7,497,844 B2 | 3/2009 | Spear et al. |
| 7,985,232 B2 | 7/2011 | Potter et al. |
| 8,142,446 B2 | 3/2012 | Shan |
| 8,486,024 B2 | 7/2013 | Steube |
| 8,512,293 B2 | 8/2013 | Leeflang et al. |
| 2005/0192537 A1 | 9/2005 | Osborne et al. |
| 2010/0094225 A1 | 4/2010 | Hastings et al. |
| 2010/0312190 A1* | 12/2010 | Searfoss ............... A61M 39/06 604/167.04 |
| 2012/0065612 A1 | 3/2012 | Stout et al. |
| 2012/0245527 A1 | 9/2012 | Stephens et al. |
| 2013/0310765 A1 | 11/2013 | Stephens et al. |

FOREIGN PATENT DOCUMENTS

| | | |
|---|---|---|
| JP | 2008529672 A | 8/2008 |
| JP | 2010508905 A | 3/2010 |
| WO | WO9906099 A2 | 2/1999 |
| WO | 2009041522 A1 | 4/2009 |
| WO | 2015085123 A1 | 6/2015 |

OTHER PUBLICATIONS

International Search Report and Written Opinion issued in PCT/US2014/068673, dated Apr. 22, 2015, 11 pages.

\* cited by examiner

CUTTABLE CATHETER HUB WITH INTEGRATED HEMOSTASIS VALVE

CROSS-REFERENCE TO RELATED APPLICATION

This application claims priority to Provisional Application No. 61/912,376, filed Dec. 5, 2013, which is herein incorporated by reference in its entirety.

TECHNICAL FIELD

The present disclosure relates generally to the field of medical instruments, and more particularly to catheter hemostasis hubs and valves for use in catheterization and related procedures.

BACKGROUND

Various medical procedures require the introduction of one or more medical instruments into arteries or veins so that the medical instruments may be advanced to a body location requiring diagnosis or treatment. For example, a guide catheter may be advanced through the patient's vasculature for delivery of a cardiac lead to a desired treatment location, such as the coronary venous system. A hub with a Luer fitting is typically coupled to the proximal end of the catheter to facilitate manipulation (e.g., rotation and translation) of the catheter by the clinician. Additionally, a hemostasis valve is further typically coupled to the hub and operates to control or inhibit the flow of blood out of the guide catheter lumen. A medical electrical lead or other device (e.g., a guide wire) may be inserted through the hemostasis valve, the hub, and the guide catheter lumen into the patient's vasculature, with the hemostasis valve operating to inhibit blood flow around the lead.

There exists a continuing need for improved hemostasis valves and catheter hubs that can facilitate removal of the catheter from the patient's body while leaving the lead in place in the patient's body.

SUMMARY

In Example 1, a catheter hemostasis valve hub comprising a tubular shell, a hemostasis seal, and an end cap. The tubular shell has an outer wall, and an internal lumen enclosed by an inner surface of the outer wall extending axially through the shell. The outer wall includes a first region having a first thickness and a second region having a second thickness greater than the first thickness. The hemostasis seal is disposed within the shell and extends across the internal lumen and fluidly isolates from an external environment a portion of the internal lumen distal to the hemostasis seal. The hemostasis seal has a bore generally aligned with the internal lumen of the shell and a slit extending axially through the hemostasis seal, the slit having a first segment extending radially from the bore toward the first region of the shell and terminating radially inward of the inner surface of the shell outer wall. The end cap is disposed within the shell proximal to the hemostasis seal so as to retain the hemostasis seal within the shell. The end cap has an elongated bore extending axially therethrough having a first portion substantially coaxially aligned with the internal lumen of the shell and a second portion extending radially from the first portion toward second region of the outer wall of the shell.

In Example 2, the catheter hemostasis valve hub of Example 1, wherein the bore of the hemostasis seal includes a first end terminating at the proximal face having a first width, a second end opposite the first end, and a chamber extending between the first and second ends having a second width generally parallel to the first width, wherein the first width is less than the second width.

In Example 3, the catheter hemostasis valve hub of either of Examples 1 or 2, wherein the inner surface of the outer wall includes a first shoulder extending radially inward, the first shoulder including a proximal surface having a generally annular shape, the proximal surface including a raised ridge in the second region of the shell defining an annular groove between the ridge and the outer wall, the hemostasis seal having an annular protrusion extending distally therefrom, the annular protrusion fitted in the groove so as to retain the hemostasis seal within the shell.

In Example 4, the catheter hemostasis valve hub of any of Examples 1-3, wherein the inner surface of the outer wall includes at least one notch in the second region of the shell, and wherein the hemostasis seal further includes at least one projection extending radially outward, the at least one notch receiving the at least one projection.

In Example 5, a catheter hemostasis valve hub comprising a tubular shell, a hemostasis seal, and an end cap. The tubular shell has an outer wall, an open proximal end, an open distal end opposite the proximal end, and an internal lumen enclosed by an inner surface of the outer wall extending through the distal end. The outer wall further includes a first region having a first thickness and a second region having a second thickness greater than the first thickness. The hemostasis seal is disposed within the shell between the proximal and distal ends of the shell, the hemostasis seal further extending across the internal lumen and fluidly isolating from an external environment a portion of the internal lumen distal to the hemostasis seal. The hemostasis seal has a proximal face, an opposite distal face, an outer perimeter, a bore originating in the proximal face and extending toward the distal face, and a slit extending axially through the hemostasis seal from the proximal face to the distal face. The slit has a first segment extending radially from the bore toward the first region of the shell and terminating radially inward of the outer perimeter. The end cap is disposed within the shell proximal to the hemostasis seal so as to retain the hemostasis seal within the shell. The end cap has a perimeter and an elongated bore extending therethrough, the elongated bore having a first portion substantially coaxially aligned with the internal lumen of the shell and a second portion extending radially from the first portion toward the perimeter of the end cap, the second portion terminating radially inward of the perimeter of the end cap so as to define a web section. The web section is positioned adjacent to the first region of the shell.

In Example 6, the catheter hemostasis valve hub of Example 5, wherein the bore of the hemostasis seal includes a first end terminating at the proximal face having a first width, a second end terminating proximal to the distal face, and a chamber extending between the first and second ends having a second width generally parallel to the first width. The first width is less than the second width.

In Example 7, the catheter hemostasis valve hub of any of Examples 5-6, wherein the inner surface of the outer wall includes a first shoulder extending radially inward, the first shoulder including a proximal surface having a generally annular shape, the proximal surface including a raised ridge in the second region of the shell defining an annular groove between the ridge and the outer wall, the distal face of the hemostasis seal having an annular protrusion extending distally, the annular protrusion fitted in the groove so as to retain the hemostasis seal between the proximal and distal ends of the shell.

In Example 8, the catheter hemostasis valve hub of any of Examples 5-7, wherein the inner surface of the outer wall includes at least one notch in the second region of the shell, the outer perimeter of the hemostasis seal further including at least one projection extending radially outward, the at least one notch receiving the at least one projection.

In Example 9, the catheter hemostasis valve hub of any of Examples 5-8, wherein the inner surface of the outer wall includes at least one projection in the second region of the shell extending radially inward. The perimeter of the end cap includes at least one notch. The at least one notch is adapted to receive the at least one projection.

In Example 10, the catheter hemostasis valve hub of any of Examples 5-9, wherein the shell is tapered at the distal end thereof, and wherein the open distal end of the shell is configured to receive a catheter shaft having a catheter shaft lumen in fluid connection with the internal lumen of the shell.

In Example 11, the catheter hemostasis valve hub of any of Examples 5-10, wherein the slit includes a second segment extending radially from the bore toward the second region of the shell.

In Example 12, the catheter hemostasis valve hub of any of Examples 5-11, wherein the end cap includes at least one leg extending distally from the end cap and disposed between the seal and the outer wall, the outer wall of the shell including a slot having a proximal opening, the leg fitted into the slot.

In Example 13, a guide catheter comprising a guide catheter shaft and a hemostasis valve hub secured to the guide catheter shaft. The guide catheter shaft includes a guide catheter lumen, and the hemostasis valve hub includes a cuttable tubular shell, a cuttable, one-piece hemostasis seal, and a cuttable end cap. The tubular shell has an outer wall, an open proximal end, an open distal end opposite the proximal end, and an internal lumen enclosed by an inner surface of the outer wall extending through the distal end. The outer wall further includes a first region having a first thickness and a second region having a second thickness greater than the first thickness to facilitate a smooth cutting transition when cutting from the hemostasis valve hub to the guide catheter shaft through the first region. A proximal end of the guide catheter shaft is disposed within the open distal end of the shell. The hemostasis seal is disposed within the shell between the proximal and distal ends of the shell. The hemostasis seal further extends across the internal lumen and fluidly isolates from an external environment a portion of the internal lumen distal to the hemostasis seal. The hemostasis seal has a proximal face, an opposite distal face, an outer perimeter, a bore originating in the proximal face and extending toward the distal face, and a slit extending axially through the hemostasis seal from the proximal face to the distal face, the slit having a first segment extending radially from the bore toward the first region of the shell and terminating radially inward of the outer perimeter. The end cap is disposed within the shell proximal to the hemostasis seal so as to retain the hemostasis seal within the shell. The end cap has a perimeter and an elongated bore extending therethrough, the elongated bore having a first portion substantially coaxially aligned with the internal lumen of the shell and a second portion extending radially from the first portion toward the perimeter of the end cap, the second portion terminating radially inward of the perimeter of the end cap so as to define a web section. The web section is positioned adjacent to the first region of the shell.

In Example 14, the guide catheter of Example 13, wherein the bore of the hemostasis seal includes a first end terminating at the proximal face having a first width, a second end terminating proximal to the distal face, and a chamber extending between the first and second ends having a second width generally parallel to the first width, wherein the first width is less than the second width.

In Example 15, the guide catheter of either of Examples 13 or 14, wherein the inner surface of the outer wall includes a first shoulder extending radially inward, the first shoulder including a proximal surface having a generally annular shape, the proximal surface including a raised ridge in the second region of the shell defining an annular groove between the ridge and the outer wall, the distal face of the hemostasis seal having an annular protrusion extending distally, the annular protrusion fitted in the groove so as to retain the hemostasis seal between the proximal and distal ends of the shell.

In Example 16, the guide catheter of any of Examples 13-15, wherein the inner surface of the outer wall includes at least one notch in the second region of the shell, the outer perimeter of the hemostasis seal further including at least one projection extending radially outward, the at least one notch receiving the at least one projection.

In Example 17, the guide catheter of any of Examples 13-16, wherein the inner surface of the outer wall includes at least one projection in the second region of the shell extending radially inward, the perimeter of the end cap including at least one notch, the at least one notch adapted to receive the at least one projection.

In Example 18, the guide catheter of any of Examples 13-17, wherein the end cap includes a Luer fitting extending proximally from the end cap. The Luer fitting has a lumen extending therethrough and is coaxially aligned with the internal lumen of the tubular shell. The Luer fitting is configured to facilitate flushing and aspirating of the guide catheter therethrough. The Luer fitting is further configured to couple to a syringe such that when the syringe is coupled, the syringe is configured to support manipulating and torqueing of the guide catheter.

In Example 19, the guide catheter of any of Examples 13-18, wherein the tubular shell includes a handle extending radially outward from the second region configured to facilitate manipulating and torqueing of the guide catheter.

In Example 20, the guide catheter of Example 19, wherein the handle includes a lumen extending through the handle. The lumen has a first end fluidly connected to the isolated portion of the internal lumen and a second end adapted to receive a tube. The tube has a lumen extending therethrough with a first end fluidly connected to the handle lumen and a second end fluidly connected to a flush port having a Luer fitting. The flush port is configured to facilitate flushing and aspirating of the guide catheter therethrough. The Luer fitting is configured to couple to a syringe.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Figure 1:
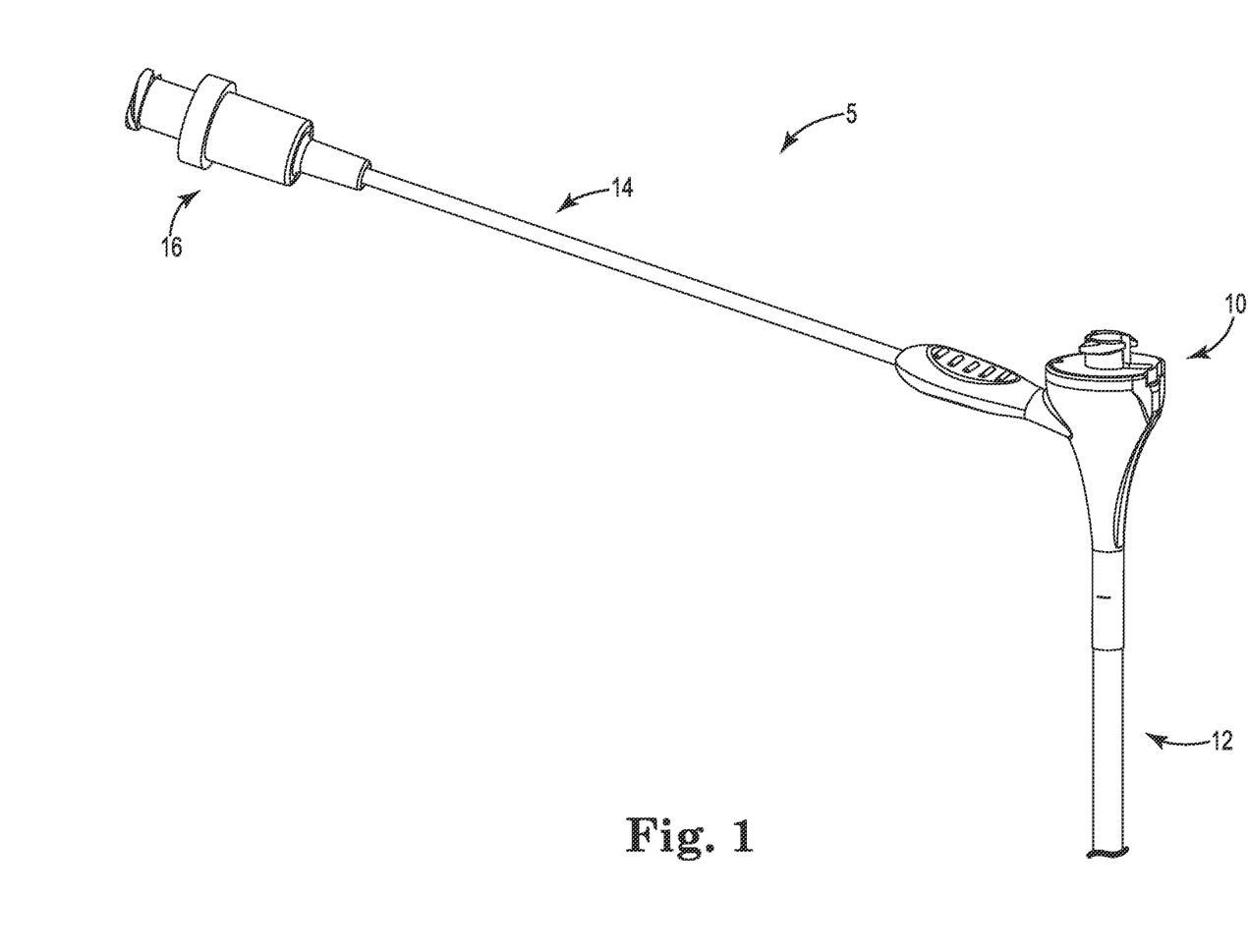
FIG. 1 is an isometric view of a portion of an exemplary guide catheter including a catheter hemostasis valve hub and a catheter shaft.

FIG. 1 is an isometric view of a portion of an exemplary guide catheter 5 according to one embodiment. As shown, the guide catheter 5 can include a hemostasis valve hub 10 and a catheter shaft 12 extending distally from the hemostasis valve hub 10. In various embodiments, the guide catheter 5 may be used in any medical procedure requiring catheterization. The guide catheter 5 can be any catheter, whether now known or later developed, for use in delivery and/or deployment of implantable medical devices (e.g., medical electrical leads, stents, and implantable sensors) or other catheterization procedures (e.g., drug delivery, mapping, and ablation). In various embodiments, the guide catheter 5 can include at least one internal lumen (not shown in FIG. 1) through which the implantable medical device (e.g., lead) and other therapeutic materials (e.g. drugs, biological materials, and the like) can be introduced into the patient's vasculature. In various embodiments, the guide catheter 5 is of a type configured for accessing and cannulating the coronary sinus and branch vessels thereof for delivery of cardiac leads for left ventricular pacing. In various embodiments, a lead can extend through the guide catheter 5 and the hemostasis valve hub 10 for delivery to and fixation within the patient's heart or coronary venous system. In various embodiments, the guide catheter 5 may be an outer guide catheter, and a smaller diameter inner catheter may be extended through hemostasis valve hub 10 and the guide catheter 5. In the latter embodiments, the inner catheter may itself include a hemostasis valve hub, which may be similar or identical to the hemostasis valve hub 10 coupled to one of its ends.

As will be explained in greater detail elsewhere herein, the hemostasis valve hub 10 can include a seal adapted to inhibit the flow of blood or other bodily fluids out of the guide catheter 5 and to maintain a substantially positive fluid seal around a medical electrical lead (or other device such as, for example, an inner catheter, or guidewire) extending through the hemostasis valve hub 10. Additionally, the hemostasis valve hub 10 is configured to allow the seal to permit a lead, catheter, or other device to be advanced through the hemostasis valve hub 10 without excessive resistance. Still additionally, the hemostasis valve hub 10 is readily cuttable or slittable through its length, facilitating a smooth transition when cutting from the hemostasis valve hub 10 to a catheter shaft 12.

In the illustrated embodiment, the hemostasis valve hub 10 can include a flush tube 14 and a flush port 16 having a Luer fitting. In other embodiments, the flush tube 14 and/or the flush port 16 may be omitted or take on a different configuration than that shown. When present, the flush tube 14 and flush port 16 are operable to allow for the introduction of fluids, e.g., sterilized water, heparinized saline, and the like, to purge the guide catheter 5 of air and/or to flush the inner lumen during use. In general, the flush tube 14 and flush port 16 may facilitate flushing or aspirating the guide catheter 5. A mechanism, such as a syringe, may be attached to the Luer fitting of the flush port 16 to facilitate such flushing or aspirating.

In various embodiments, the catheter shaft 12 can be joined to the hemostasis valve hub 10 using any suitable joining technique, whether now known or later developed. In various embodiments, these components may be joined by an adhesive or by mechanical joining techniques such as, for example, heat fusing, laser welding, or ultrasonic welding. Similarly, the hemostasis valve hub 10, flush tube 14, and flush port 16 may be coupled together using any suitable method, including adhesive and mechanical joining techniques such as heat fusing, welding, and the like.

Figure 2:
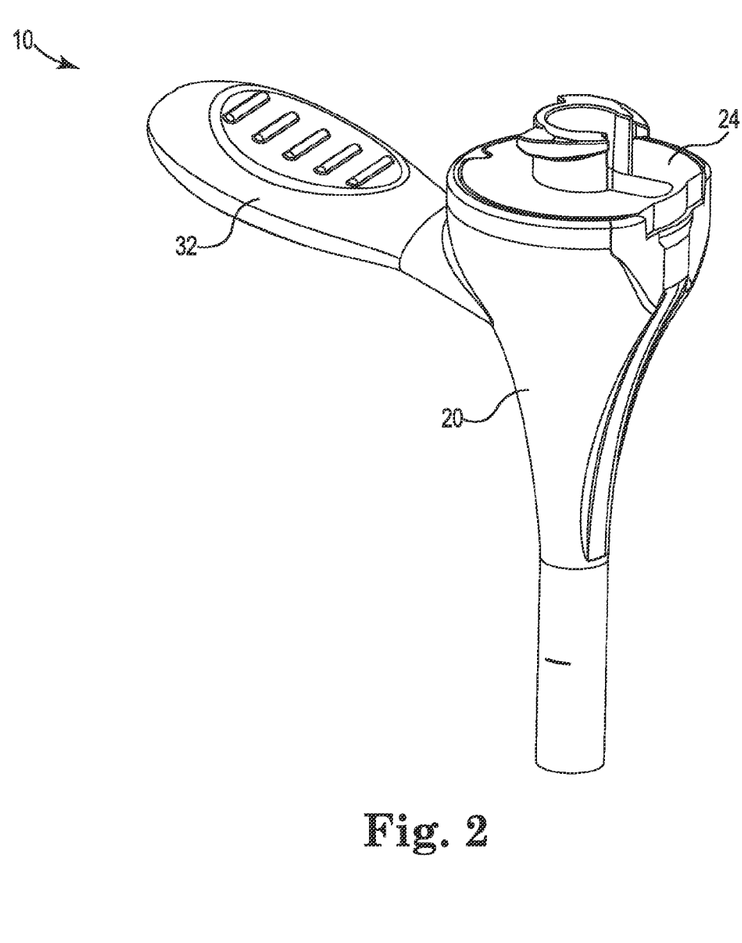
FIG. 2 is an isometric view of an assembled catheter hemostasis valve hub according to various embodiments of the present disclosure.
Figure 3:
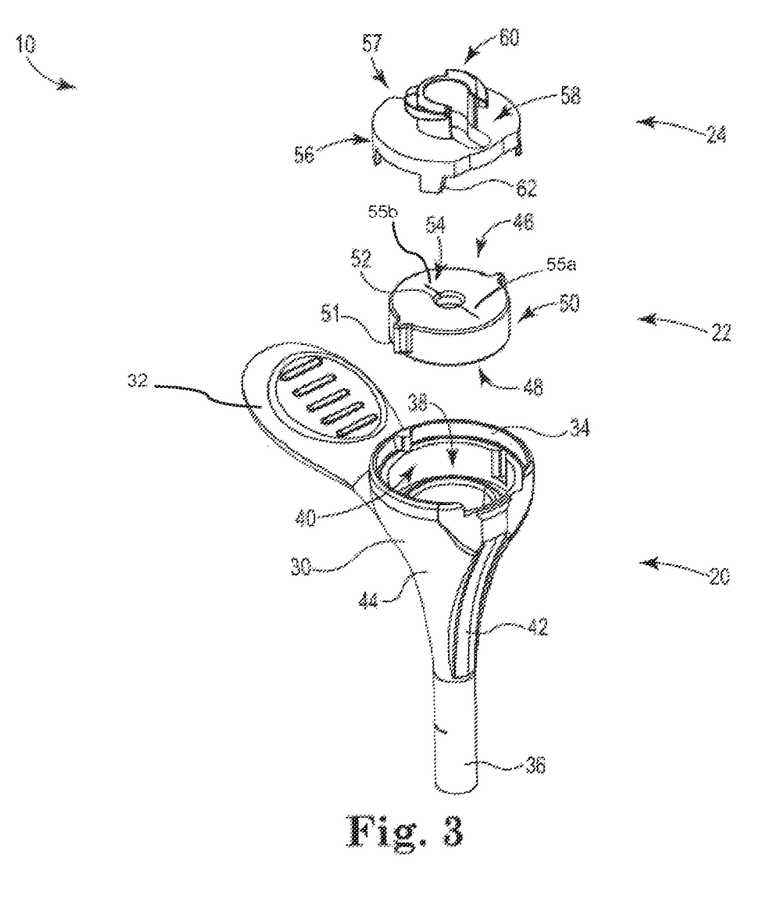
FIG. 3 is an isometric exploded view of the catheter hemostasis valve hub of FIG. 2 showing a generally tubular shell, a hemostasis seal, and an end cap according to various embodiments of the present disclosure.
Figure 4:
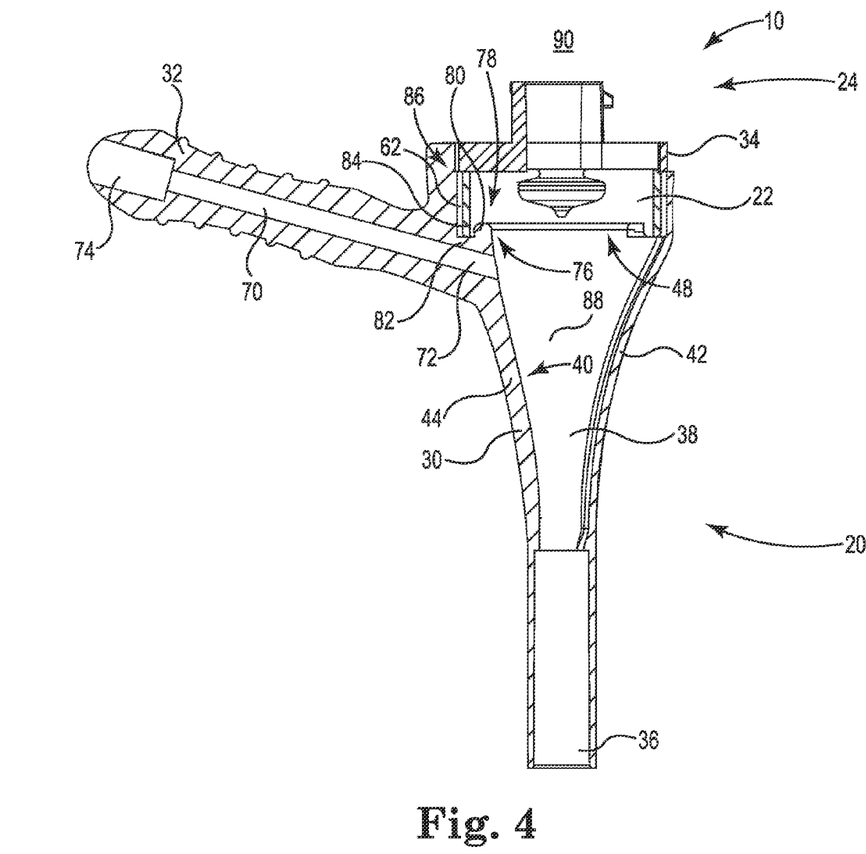
FIG. 4 is a cross-sectional elevation view of the assembled hub of FIG. 2.

FIGS. 2 and 3 are isometric assembled and exploded views, respectively, of the hemostasis valve hub 10, and FIG. 4 is a cross-sectional elevation view of the hemostasis valve hub 10 according to one embodiment. As shown in FIGS. 2-4, collectively, the hemostasis valve hub 10 includes a generally tubular shell 20, a hemostasis seal 22, an end cap 24 and a handle 32. In the illustrated embodiment, the flush tube 14 and flush port 16 (see FIG. 1) are omitted, but in various embodiments these features can also be included.

As can be seen in FIGS. 2-4, when assembled, the hemostasis seal 22 is disposed within the shell 20 and the end cap 24 is disposed within the shell 20 proximal to the hemostasis seal 22 so as to retain the hemostasis seal 22 within the shell 20.

As shown, the shell 20 can include an outer wall 30, an open proximal end 34, an open distal end 36 opposite the proximal end, and an internal lumen 38 enclosed by an inner surface 40 of the outer wall 30 extending through the distal end 36. The outer wall 30 of the shell 20 can further include a first region 42 and a second region 44. In the illustrated embodiment, the outer wall 30 of the shell 20 is tapered at the distal end 36 so as to be fitted to a guide catheter shaft 12 (see FIG. 1). In the various embodiments, the internal lumen 38 is generally aligned with an internal lumen of the catheter shaft 12. The shell 20 may be made of any suitable resilient material, such as a polyether block amide or other comparable polymer material. In one embodiment, the shell 20 is made of a polyether block amide sold under the brand name PEBAX having a Shore hardness of 55D-75D.

In the various embodiments, the first region 42 of the outer wall 30 has a first thickness 43, and the second region 44 of the outer wall 30 has a second thickness 45 greater than the first thickness 43. A relatively thin first thickness 43 facilitates cutting or slitting the shell 20 through the first region 42 and a smooth transition to cutting the catheter shaft 12 during removal of the guide catheter 5 from the patient with a payload (e.g., a pacing lead) disposed within the lumen of the guide catheter 5. The first thickness 43, which is thinner than the second thickness 45, may be defined as a cutting zone, because the first thickness 43 is more easily cut than the rest of the outer wall 30 of the shell 20, which facilitates the smooth transition to the guide catheter 5.

As shown, the hemostasis seal 22 can include a proximal face 46, an opposite distal face 48, an outer perimeter 50, a bore 52 originating in the proximal face 46 and extending toward the distal face 48, and a slit 54 extending axially through the hemostasis seal 22 from the proximal face 46 to the distal face 48. The slit 54 may include a first segment 55a and a second segment 55b. As shown, the first segment 55a extends radially from the bore 52 toward the first region 42 of the shell 20 and terminates radially inward of the outer perimeter 50. Additionally, the second segment 55b extends radially from the bore 52 toward the second region 44 of the shell 20 and terminates radially inward of the outer perimeter 50. The outer perimeter 50 of the hemostasis seal 22 may include one or more projections 51 extending radially outward. The hemostasis seal 22 may be made of any suitable resilient material, such as silicone.

The end cap 24 can include a perimeter 56 and an elongated bore 58 extending therethrough. The end cap 24 can further include a Luer fitting 60 extending proximally from the end cap 24 to enable in-line attachment of a delivery mechanism (e.g. syringe) and one or more legs 62 near the perimeter 56. Mechanisms for flushing or aspirating may also be attached to the Luer fitting 60 to enable a fluid connection to the elongated bore 58, such as a syringe. When attached to the Luer fitting 60, such mechanisms may also be used to support the manipulation of or application of torque to the guide catheter 5. As utilized herein, the application of torque may be considered one manner of manipulating the guide catheter 5. The perimeter 56 of the end cap 24 can also include a notch 57. The end cap 24 may be made of any suitable material, such as PEBAX or comparable polymer material. In one embodiment, the end cap 24 is made of PEBAX having a hardness of 63D.

As further shown, in the illustrated embodiment, the handle 32 extends radially outward from the second region 44 to facilitate manipulation of the guide catheter 5. The handle 32 may also be used to apply torque to the guide catheter 5. As can be seen in FIG. 4, in the particular embodiment shown, the shell 20 can further include a flush port lumen 70 extending through the handle 32. The flush port lumen 70 has a first end 72 fluidly connected to the internal lumen 38 and a second end 74 adapted to receive the flush tube 14. In various embodiments not shown, the shell 20 does not include the handle 32.

As shown, the inner surface 40 of the outer wall 30 can include a first shoulder 76 and a second shoulder 86, each extending radially inward from the inner surface 40. The first shoulder 76 has a proximal surface 78 having a generally annular shape, which can include a raised ridge 80 in the second region 44 of the shell 20 defining a generally annular groove 82 between the ridge 80 and the outer wall 30. In the first region 42 of the shell 20, the proximal surface 78 lacks the raised ridge 80.

The hemostasis seal 22 can include an annular protrusion 84 extending distally and adapted to fit with the annular groove 82. The hemostasis seal 22 is disposed within the shell 20 between the proximal end 34 and the distal end 36 of the shell 20. The hemostasis seal 22 extends across the internal lumen 38 and fluidly isolates a portion 88 of the internal lumen 38 from an external environment 90 at the proximal end 34 of the shell 20. As shown, the isolated portion 88 is defined by the distal face 48 of the hemostasis seal 22 and the inner surface 40 of the outer wall 30.

The end cap 24 is disposed within the shell 20 proximal to the hemostasis seal 22 and abuts the second shoulder 86. The end cap 24 may be coupled to the shell 20 by any suitable method, including an adhesive attachment, heat fusing, welding (e.g., ultrasonic welding), or an interference fit, so as to retain the hemostasis seal 22 within the shell 20.

Figure 5:
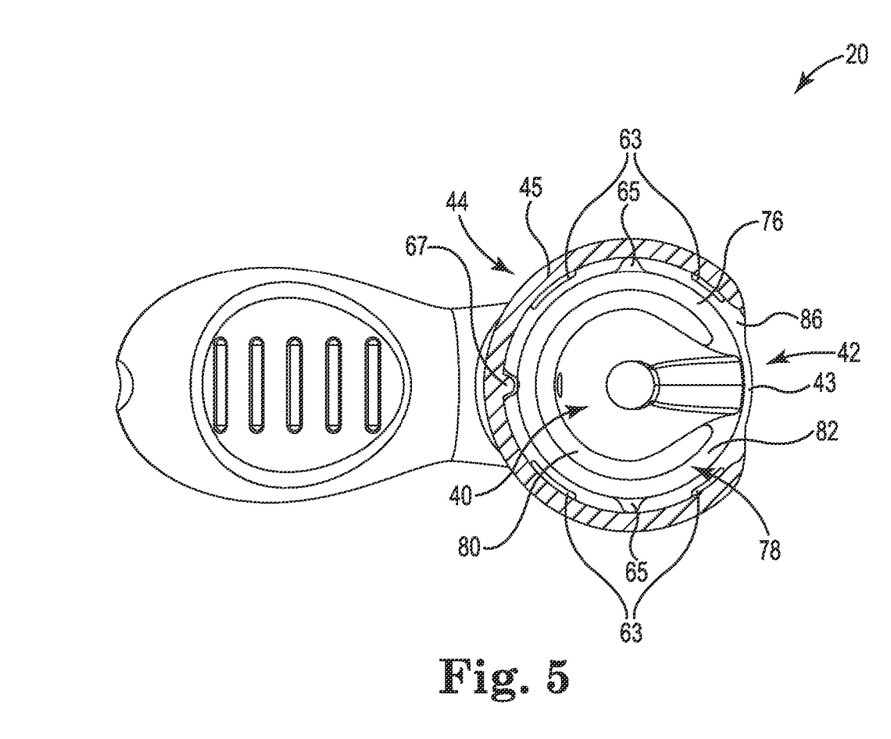
FIG. 5 is a top view of a generally tubular shell according to various embodiments of the present disclosure.

FIG. 5 is a top view of a generally tubular shell 20 according to various embodiments of the disclosure. As shown in FIG. 5, the first shoulder 76 extends radially inward forming the annular proximal surface 78. The annular proximal surface 78 can include the raised ridge 80 and annular groove 82 for receiving an annular protrusion 84. As further shown, one or more slots 63 are formed in the second shoulder 86 in the second region 44 of the shell 20 fitted to receive the one or more legs 62 of the end cap 24 so as to facilitate retention of the hemostasis seal 22 between the end cap 24 and the proximal surface 78 of the first shoulder 76 (as shown in FIG. 4). Additionally, the inner surface 40 of the outer wall 30 can include one or more notches 65 in the second region 44 of the shell 20 fitted to receive the one or more projections 51 of the hemostasis seal 22 (as shown in FIG. 3) when assembled. In various embodiments (not shown), the one or more notches 65 and the one or more projections 51 can be formed on the shell 20 and the end cap 24, respectively.

In the illustrated embodiment, the inner surface 40 can also include a projection 67 in the second region 44 of the shell 20 extending radially inward. A notch 57 in the perimeter 56 of an end cap 24 is adapted to receive the projection 67. In various embodiments (not shown), the notch 57 and projection 67 can be formed on the shell 20 and the end cap 24, respectively.

Figure 6:
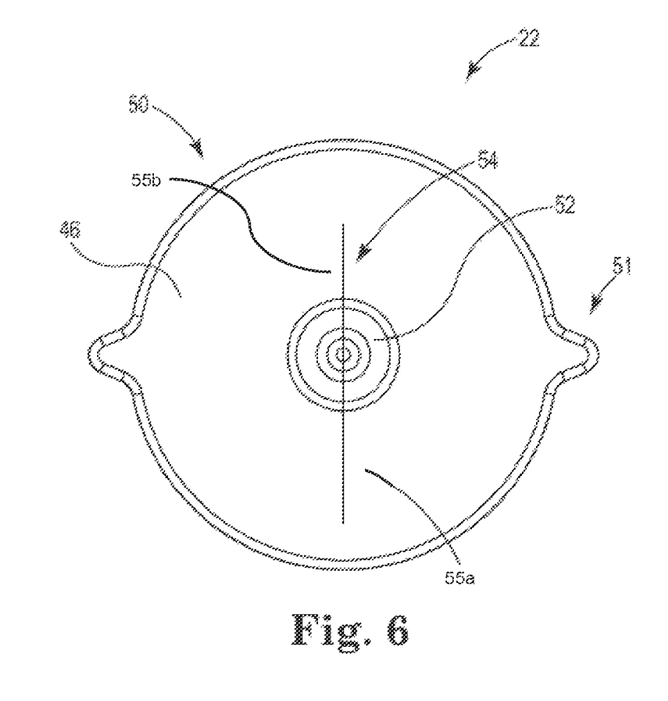
FIG. 6 is a top view of a hemostasis seal according to various embodiments of the present disclosure.
Figure 7:
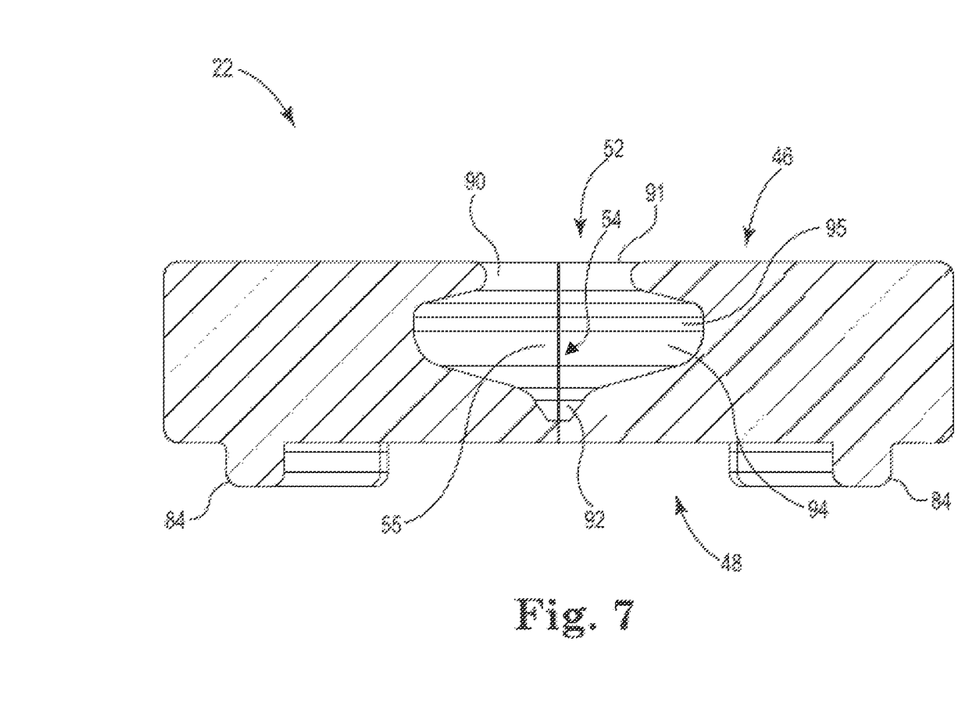
FIG. 7 is a cross-sectional side view of the hemostasis seal of FIG. 6.

FIGS. 6 and 7 are top and cross-sectional side views, respectively, of the hemostasis seal 22 according to various embodiments showing the proximal face 46, outer perimeter 50, bore 52, slit 54 including the first and second segments 55a, 55b, and the one or more projections 51 of the hemostasis seal 22. An example hemostasis seal 22 is a one-piece seal, wherein the slit 54 terminates interior to the outer perimeter 50 of the hemostasis seal and does not split the seal into two pieces. In the illustrated embodiment, the slit 54 extends radially from the bore 52 in a first direction forming the first segment 55a and a second direction opposite the first direction forming the second segment 55b. In various embodiments, the first segment 55a may have a length of about 25 percent to about 90 percent of the distance between the center of the bore 52 and the outer perimeter 50. In one embodiment, the first segment 55a has a length such that it extends about 75 percent of the distance from the center of the bore 52 to the outer perimeter 50. As further shown, in the illustrated embodiment, the length of the first segment 55a is greater than the length of the second segment 55b. In various embodiments, the second segment 55b may have a length of about 25 percent to about 75 percent of the distance between the center of the bore 52 and the outer perimeter 50. In one embodiment, the second segment 55b has a length such that it extends about 50 percent of the distance from the center of the bore 52 to the outer perimeter 50. The selected lengths of the respective segments 55a, 55b allows for optimization of the structural integrity, sealing effectiveness, and cuttability of the hemostasis seal 22.

As further shown, the bore 52 originates at the proximal surface 46 of the hemostasis seal 22 and extends toward the opposing distal face 48. The bore 52 further can include a first end 90 having a first width 91, a second end 92 terminating proximal the distal face 48 of the hemostasis seal 22, and a chamber 94 extending between the first 90 and second 92 ends having a second width 95 generally parallel to the first width 91. In the illustrated embodiment, the second width 95 is greater than the first width 91.

In various embodiments, the hemostasis seal 22 is configured to facilitate ease of cutting or slitting through the hemostasis valve hub 10. The first segment 55a extends axially through the hemostasis seal 22 from the proximal face 46 to the distal face 48 and extends radially from the bore 52 toward a first region 42 of a shell 20 when assembled. Also, the annular protrusion 84 does not form a complete ring near the outer perimeter 50. The existence of the first segment 55a of the slit 54 and of the lack of annular protrusion 84 adjacent the first segment 55a reduces the amount of material necessary to cut or slit through a portion of the hemostasis seal 22 between the bore 52 and the outer perimeter 50.

Figure 8:
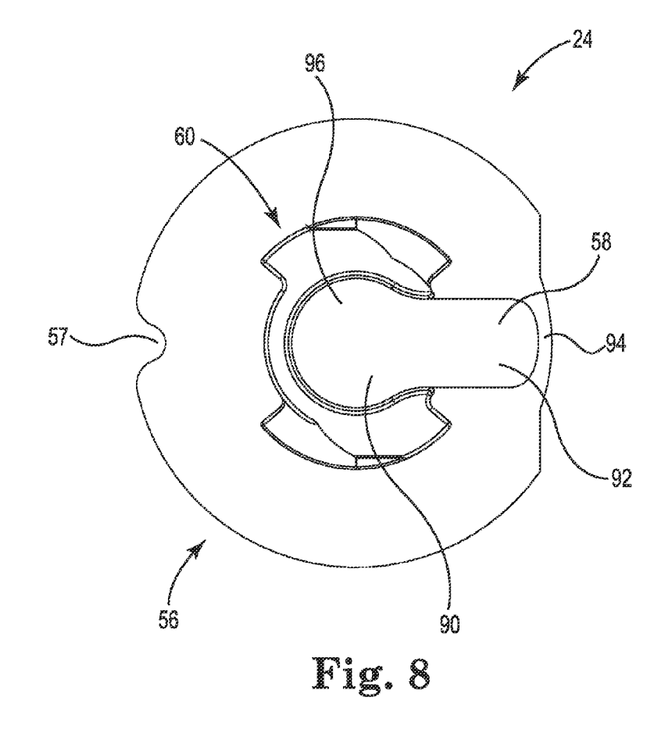
FIG. 8 is a top view of an end cap according to various embodiments of the present disclosure.
Figure 9:
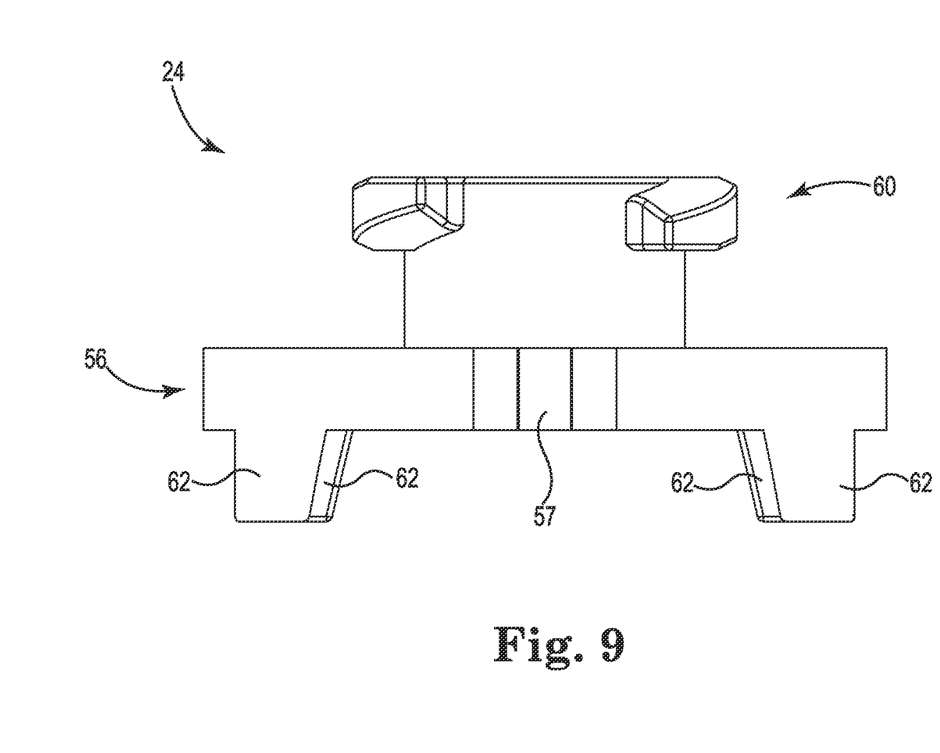
FIG. 9 is a side view of the end cap of FIG. 8.

FIGS. 8 and 9 are top and side views, respectively, of the end cap 24 according to various embodiments showing additional detail of the elongated bore 58. The elongated bore 58 can include a first portion 90 and a section portion 92, extending radially from the first portion 90 toward the perimeter 56 of the end cap 24. The second portion 92 terminates radially inward of the perimeter 56 defining a web section 94. When assembled, the first portion 90 is substantially coaxially aligned with the internal lumen 38 of the shell 20, and the web section 94 is positioned adjacent to the first region of the shell 20 to facilitate introduction of an implantable medical device or other materials. The web section 94 facilitates the ease of cutting or slitting through the end cap 24. In the illustrated embodiment, the first portion 90 has a first width and the second portion 92 has a second width generally parallel to and less than the first width of the first portion 90. The notch 57 can be formed in the perimeter 56 of the end cap 24.

The Luer fitting 60 can include a lumen 96 extending therethrough and, when assembled, coaxially aligned with the internal lumen 38 of the shell 20 to facilitate introduction of an implantable medical device or other materials. When present, mechanisms may be fluidly connected to the lumen 96 to facilitate flushing or aspirating.

As can be seen in FIG. 9, the one or more legs 62 of the end cap 24 extend distally and the Luer fitting 60 extending proximally. The notch 57 in the perimeter 56 is also shown in FIG. 9.

After introducing an implantable device into the guide catheter 5, the position of the web section 94 of the end cap 24, the first segment 55a of the slit 54 in the hemostasis seal 22, and the first region 42 of the shell 20 work together to facilitate ease of cutting or slitting through the hemostasis valve hub 10 and providing a smooth transition into cutting or slitting an attached catheter shaft 12. The introduced device can remain in place while the guide catheter 5 is then removed.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:
1. A catheter hemostasis valve hub comprising:
a tubular shell having an outer wall, an open proximal end, an open distal end opposite the proximal end, and an internal lumen enclosed by an inner surface of the outer wall extending through the distal end, the outer wall further including a first region having a first thickness and a second region having a second thickness greater than the first thickness to facilitate cutting through the first region,
wherein the first region extends between the open proximal end and the open distal end along the outer wall, and
wherein the tubular shell includes an annular groove;
a hemostasis seal disposed within the shell between the proximal and distal ends of the shell, the hemostasis seal further extending across the internal lumen and fluidly isolating from an external environment a portion of the internal lumen distal to the hemostasis seal, the hemostasis seal having a proximal face, an opposite distal face, an outer perimeter, a bore originating in the proximal face and extending toward the distal face, and a slit extending axially through the hemostasis seal from the proximal face to the distal face, the slit having a first segment extending radially from the bore toward the first region of the shell and terminating radially inward of the outer perimeter,
wherein the hemostasis seal includes annular protrusion received within the annular groove of the tubular shell, and
wherein the annular protrusion does not form a complete ring adjacent the first segment of the slit of the hemostasis seal; and
an end cap disposed within the shell proximal to the hemostasis seal so as to retain the hemostasis seal within the shell, the end cap having a perimeter and an elongated bore extending therethrough, the elongated bore having a first portion substantially coaxially aligned with the internal lumen of the shell and a second portion extending radially from the first portion toward the perimeter of the end cap, the second portion terminating radially inward of the perimeter of the end cap so as to define a web section, the web section being positioned adjacent to the first region of the shell.
2. The catheter hemostasis valve hub of claim 1, wherein the slit of the hemostasis seal is radially aligned with the web section of the end cap adjacent to the first region of the shell.
3. The catheter hemostasis valve hub of claim 1, wherein the bore of the hemostasis seal includes a first end terminating at the proximal face having a first width, a second end terminating proximal to the distal face, and a chamber extending between the first and second ends having a second width generally parallel to the first width, wherein the first width is less than the second width.
4. The catheter hemostasis valve hub of claim 1, wherein the inner surface of the outer wall includes a first shoulder extending radially inward, the first shoulder including a proximal surface having a generally annular shape, the proximal surface including a raised ridge in the second region of the shell defining an annular groove between the ridge and the outer wall, the distal face of the hemostasis seal having an annular protrusion extending distally, the annular protrusion fitted in the groove so as to retain the hemostasis seal between the proximal and distal ends of the shell.
5. The catheter hemostasis valve hub of claim 1, wherein the inner surface of the outer wall includes at least one notch in the second region of the shell, the outer perimeter of the hemostasis seal further including at least one projection extending radially outward, the at least one notch receiving the at least one projection.

6. The catheter hemostasis valve hub of claim 1, wherein the inner surface of the outer wall includes at least one projection in the second region of the shell extending radially inward, the perimeter of the end cap including at least one notch, the at least one notch adapted to receive the at least one projection.

7. The catheter hemostasis valve hub of claim 1, wherein the shell is tapered at the distal end thereof, and wherein the open distal end of the shell is configured to receive a catheter shaft having a catheter shaft lumen in fluid connection with the internal lumen of the shell.

8. The catheter hemostasis valve hub of claim 1, wherein the slit includes a second segment extending radially from the bore toward the second region of the shell.

9. The catheter hemostasis valve hub of claim 1, wherein the end cap includes at least one leg extending distally from the end cap and disposed between the seal and the outer wall, the outer wall of the shell including a slot having a proximal opening, the leg fitted into the slot.

10. A guide catheter comprising:
a guide catheter shaft including a guide catheter lumen; and
a hemostasis valve hub secured to the guide catheter shaft, the hemostasis valve hub including:
a cuttable tubular shell having an outer wall, an open proximal end, an open distal end opposite the proximal end, and an internal lumen enclosed by an inner surface of the outer wall extending through the distal end, the outer wall further including a first region having a first thickness and a second region having a second thickness greater than the first thickness to facilitate a smooth cutting transition when cutting from the hemostasis valve hub to the guide catheter shaft through the first region,
wherein the first region extends between the open proximal end and the open distal end along the outer wall,
wherein a proximal end of the guide catheter shaft is disposed within the open distal end of the shell, and
wherein the tubular shell includes an annular groove;
a cuttable, one-piece hemostasis seal disposed within the shell between the proximal and distal ends of the shell, the hemostasis seal further extending across the internal lumen and fluidly isolating from an external environment a portion of the internal lumen distal to the hemostasis seal, the hemostasis seal having a proximal face, an opposite distal face, an outer perimeter, a bore originating in the proximal face and extending toward the distal face, and a slit extending axially through the hemostasis seal from the proximal face to the distal face, the slit having a first segment extending radially from the bore toward the first region of the shell and terminating radially inward of the outer perimeter,
wherein the hemostasis seal includes annular protrusion received within the annular groove of the tubular shell, and
wherein the annular protrusion does not form a complete ring adjacent the first segment of the slit of the hemostasis seal; and
a cuttable end cap disposed within the shell proximal to the hemostasis seal so as to retain the hemostasis seal within the shell, the end cap having a perimeter and an elongated bore extending therethrough, the elongated bore having a first portion substantially coaxially aligned with the internal lumen of the shell and a second portion extending radially from the first portion toward the perimeter of the end cap, the second portion terminating radially inward of the perimeter of the end cap so as to define a web section, the web section being positioned adjacent to the first region of the shell.

11. The guide catheter of claim 10, wherein the bore of the hemostasis seal includes a first end terminating at the proximal face having a first width, a second end terminating proximal to the distal face, and a chamber extending between the first and second ends having a second width generally parallel to the first width, wherein the first width is less than the second width.

12. The guide catheter of claim 10, wherein the inner surface of the outer wall includes a first shoulder extending radially inward, the first shoulder including a proximal surface having a generally annular shape, the proximal surface including a raised ridge in the second region of the shell defining an annular groove between the ridge and the outer wall, the distal face of the hemostasis seal having an annular protrusion extending distally, the annular protrusion fitted in the groove so as to retain the hemostasis seal between the proximal and distal ends of the shell.

13. The guide catheter of claim 10, wherein the inner surface of the outer wall includes at least one notch in the second region of the shell, the outer perimeter of the hemostasis seal further including at least one projection extending radially outward, the at least one notch receiving the at least one projection.

14. The guide catheter of claim 10, wherein the inner surface of the outer wall includes at least one projection in the second region of the shell extending radially inward, the perimeter of the end cap including at least one notch, the at least one notch adapted to receive the at least one projection.

15. The guide catheter of claim 10, wherein the end cap includes a Luer fitting extending proximally from the end cap, the Luer fitting having a lumen extending therethrough and coaxially aligned with the internal lumen of the tubular shell, the Luer fitting configured to facilitate flushing and aspirating of the guide catheter therethrough, the Luer fitting further configured to couple to a syringe such that when the syringe is coupled, the syringe is configured to support manipulating and torqueing of the guide catheter.

16. The guide catheter of claim 10, wherein the tubular shell includes a handle extending radially outward from the second region configured to facilitate manipulating and torqueing of the guide catheter.

17. The guide catheter of claim 16, the handle includes a lumen extending through the handle, the lumen having a first end fluidly connected to an isolated portion of the internal lumen and a second end adapted to receive a tube, the tube having a lumen extending therethrough with a first end fluidly connected to the handle lumen and a second end fluidly connected to a flush port having a Luer fitting, the flush port configured to facilitate flushing and aspirating of the guide catheter therethrough, the Luer fitting configured to couple to a syringe.

18. The guide catheter of claim 10, wherein the slit of the hemostasis seal is radially aligned with the web section of the end cap adjacent to the first region of the shell.

* * * * *